United States Patent
Isaacson et al.

(10) Patent No.: US 10,682,499 B2
(45) Date of Patent: Jun. 16, 2020

(54) SAFETY INTRAVENOUS CATHETER WITH FRICTION-BASED RETENTION AND DISABLING FEATURE

(71) Applicant: Becton, Dickinson and Company, Franklin Lakes, NJ (US)

(72) Inventors: S. Ray Isaacson, Layton, UT (US); Siddarth Shevgoor, Laguna Beach, CA (US); Jeff O'Bryan, Murray, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 35 days.

(21) Appl. No.: 15/698,188

(22) Filed: Sep. 7, 2017

(65) Prior Publication Data

US 2017/0368314 A1 Dec. 28, 2017

Related U.S. Application Data

(63) Continuation of application No. 14/599,402, filed on Jan. 16, 2015, now Pat. No. 9,827,400.

(30) Foreign Application Priority Data

Jan. 2, 2015 (GB) .................................. 1500012.8

(51) Int. Cl.
*A61M 25/06* (2006.01)
*A61M 25/00* (2006.01)

(52) U.S. Cl.
CPC .... *A61M 25/0625* (2013.01); *A61M 25/0097* (2013.01); *A61M 25/0618* (2013.01); *A61M 25/0637* (2013.01); *A61M 25/0693* (2013.01)

(58) Field of Classification Search
CPC .......... A61M 25/0097; A61M 25/0618; A61M 25/0625; A61M 25/0637; A61M 25/0693
See application file for complete search history.

(56) References Cited

U.S. PATENT DOCUMENTS

| | | | |
|---|---|---|---|
| 4,231,367 A | 11/1980 | Rash | |
| 5,051,109 A | 9/1991 | Simon | |
| 5,053,004 A * | 10/1991 | Markel | ............... A61M 5/1582 29/428 |
| 5,279,591 A | 1/1994 | Simon | |

(Continued)

FOREIGN PATENT DOCUMENTS

| | | |
|---|---|---|
| CN | 101466431 A | 6/2009 |
| CN | 101843947 A | 9/2010 |

(Continued)

*Primary Examiner* — Brandy S Lee
(74) *Attorney, Agent, or Firm* — Dickinson Wright PLLC (57) ABSTRACT

A catheter and introducer needle assembly, including a flexible catheter and a catheter hub having an outer surface portion. The assembly includes an introducer needle disposed in the catheter, a needle shield having a resilient clip adapted to flex between first and second positions. The resilient clip includes a cantilevered arm with a pawl. In the resilient clip's first position, the cantilevered arm is flexed so that the pawl frictionally contacts the catheter hub's outer surface portion to retain the needle shield with the catheter hub. In the second position, the pawl no longer frictionally contacts the hub's outer surface, thereby permitting needle shield displacement relative to the catheter hub.

20 Claims, 11 Drawing Sheets

(56) References Cited

U.S. PATENT DOCUMENTS

| | | |
|---|---|---|
| 5,395,347 A | 3/1995 | Blecher et al. |
| 5,718,688 A | 2/1998 | Wozencroft |
| 5,735,827 A | 4/1998 | Adwers et al. |
| 6,077,244 A | 6/2000 | Botich et al. |
| 6,234,999 B1 | 5/2001 | Wemmert et al. |
| 6,527,747 B2 | 3/2003 | Adams et al. |
| 6,629,959 B2 | 10/2003 | Kuracina et al. |
| 6,749,588 B1 * | 6/2004 | Howell ............... A61M 5/3273 604/110 |
| 7,524,306 B2 | 4/2009 | Botich et al. |
| 7,604,616 B2 | 10/2009 | Thoresen et al. |
| 7,722,569 B2 | 5/2010 | Soderholm et al. |
| 2003/0114797 A1 | 6/2003 | Vaillancourt et al. |
| 2004/0162525 A1 | 8/2004 | Vaillancourt et al. |
| 2004/0204681 A1 * | 10/2004 | Thoresen ............ A61M 5/3273 604/164.08 |
| 2004/0236287 A1 | 11/2004 | Swenson et al. |
| 2007/0270754 A1 | 11/2007 | Soderholm et al. |
| 2008/0065015 A1 | 3/2008 | Fiser et al. |
| 2008/0140004 A1 | 6/2008 | Thorne et al. |
| 2008/0140011 A1 | 6/2008 | Hager et al. |
| 2008/0147009 A1 | 6/2008 | Nilsson et al. |
| 2009/0182280 A1 | 7/2009 | Glowacki et al. |
| 2011/0054403 A1 | 3/2011 | Tanabe et al. |
| 2011/0160671 A1 | 6/2011 | Tanabe et al. |
| 2013/0090608 A1 * | 4/2013 | Stout ............... A61M 25/0097 604/256 |
| 2014/0364809 A1 | 12/2014 | Isaacson et al. |

FOREIGN PATENT DOCUMENTS

| | | |
|---|---|---|
| CN | 101868269 A | 10/2010 |
| CN | 103998090 A | 8/2014 |
| CN | 203816045 U | 9/2014 |
| DE | 202009013213 U1 | 1/2010 |
| EP | 0554841 A1 | 11/1993 |
| EP | 0510187 B1 | 2/1998 |
| EP | 1250943 B1 | 9/2004 |
| EP | 2260894 A1 | 12/2010 |
| EP | 2260896 A1 | 12/2010 |
| EP | 1920796 B1 | 8/2012 |
| EP | 2319556 B1 | 4/2013 |
| GB | 2508466 B | 6/2014 |
| GB | 2508570 B | 6/2014 |
| JP | S53-61187 | 6/1978 |
| JP | 2010-510035 A | 4/2010 |
| JP | U-3170612 | 9/2011 |
| JP | 2012-517326 A | 8/2012 |
| JP | 5352579 B2 | 11/2013 |
| WO | WO-2007/0944898 A2 | 8/2007 |
| WO | WO-2011/038931 A1 | 4/2011 |
| WO | WO-2011/154797 A3 | 12/2011 |
| WO | WO-2012/038900 A1 | 3/2012 |
| WO | WO-2012/075402 A1 | 6/2012 |

* cited by examiner

SAFETY INTRAVENOUS CATHETER WITH FRICTION-BASED RETENTION AND DISABLING FEATURE

CROSS-REFERENCE TO RELATED APPLICATION

This application is a continuation of U.S. patent application Ser. No. 14/599,402, filed Jan. 16, 2015, which claims priority to United Kingdom patent application No. 1500012.8, filed Jan. 2, 2015. The disclosure of each of these applications is hereby incorporated herein by reference in its entirety.

FIELD OF THE INVENTION

The present invention relates to intravenous catheters, and more particularly, to an intravenous catheter with friction-based retention between a catheter hub and a needle shield.

BACKGROUND OF THE INVENTION

Catheters, particularly intravenous (IV) catheters, are used for infusing fluid (such as normal saline solution, various medicaments, and total parenteral nutrition) into a patient, withdrawing blood from a patient, or monitoring various parameters of the patient's vascular system. Peripheral IV catheters tend to be relatively short, and typically are on the order of about two inches or less in length. The most common type of IV catheter is an over-the-needle peripheral IV catheter. As its name implies, an over-the-needle catheter is mounted over a hollow introducer needle having a sharp distal tip. At least the distal portion of the catheter tightly engages the outer surface of the needle to prevent peelback of the catheter and thus facilitates insertion of the catheter into the blood vessel. The catheter and the introducer needle are assembled so that the sharp distal tip of the introducer needle extends beyond the distal tip of the catheter with the bevel of the needle facing up and away from the patient's skin.

In operation, the catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

To verify proper placement of the catheter in the blood vessel, the clinician confirms that there is flashback of blood in a flashback chamber. The flashback chamber is typically formed as part of the introducer needle hub. Once proper placement of the catheter into the blood vessel is confirmed, the clinician applies pressure to the blood vessel by pressing down on the patient's skin over the blood vessel distal of the introducer needle and the catheter. This finger pressure occludes or at least minimizes further blood flow through the introducer needle and the catheter. The clinician then withdraws the introducer needle, leaving the catheter in place, and attaches an appropriate device to the catheter. Such a device can include a fluid delivery device, a PRN device (pro re nata—i.e., "as the circumstances may require"), a deadender cap, or a blood pressure monitoring probe. Once the introducer needle is withdrawn from the catheter, the introducer needle is a blood contaminated sharp and must be properly handled and disposed of.

In recent years, there has been great concern over the contamination of clinicians with a patient's blood and recognition that blood contaminated sharps must be properly handled and disposed of to avoid an accidental needle stick. This concern has arisen because of diseases such as HIV and hepatitis, which can be transmitted by the exchange of body fluids from an infected person to another person. Contact with the body fluid of an infected person must be avoided. If an introducer needle has been used to place a catheter in a blood vessel of an infected person, the introducer needle, via its sharp distal tip, is a vehicle for the transmission of the disease. Although clinicians know of the need to properly handle blood contaminated sharps, unfortunately in certain medical environments, such as emergency situations or because of inattention or neglect, needlesticks with a contaminated introducer needle can still occur.

Because of the problem of accidental needlesticks by blood contaminated sharps, various types of needle shields have been developed. Generally, such needle shields work for their intended purpose but could be improved. For example, some needle shields are bulky, difficult to use, require special features or techniques to be operative, or may leave the sharp distal tip exposed after use until the clinician manually activates the needle shielding mechanism.

Although U.S. Pat. No. 6,749,588, which is assigned to the same assignee as the present application and which is herein incorporated by reference in its entirety, sets forth many solutions to such problems, other solutions are also desirable. Some solutions employ a projection engaging a recess or undercut to provide an interlock to keep a needle shield retained with a catheter hub, but these solutions can require detailed or intricate molding or manufacturing.

SUMMARY OF EMBODIMENTS OF THE INVENTION

It is an aspect of the present invention to provide an intravenous catheter with friction-based retention between a catheter hub and a needle shield.

The foregoing and/or other aspects of the present invention are achieved by providing a catheter and introducer needle assembly, including a flexible catheter and a catheter hub in fluid communication with the catheter, the catheter hub having an outer surface portion. The assembly also includes an introducer needle disposed in the catheter, and a needle shield. The assembly additionally includes a resilient clip adapted to flex between a first position and a second position, the resilient clip having a cantilevered arm with a pawl. In the first position of the resilient clip, the cantilevered arm of the resilient clip is flexed so that the pawl frictionally contacts the outer surface portion of the catheter hub to retain the needle shield with the catheter hub, and in the second position of the resilient clip, the pawl no longer frictionally contacts the outer surface portion, thereby permitting displacement of the needle shield relative to the catheter hub.

The foregoing and/or other aspects of the present invention are also achieved by providing a catheter and introducer needle assembly, including a catheter hub having a fluid path, and an outer surface portion; a catheter communicating with the fluid path; and an introducer needle assembly. The introducer needle assembly includes an introducer needle, a needle shield selectively disposed at the catheter hub; and a resilient clip. The introducer needle is disposed through the needle shield, the catheter hub, and the catheter. The resilient clip is movably disposed within the needle shield and has a cantilevered arm extending therefrom with a pawl at the free end of the cantilevered arm. The cantilevered arm is flexed so that the pawl frictionally contacts the outer surface portion to retain the needle shield with the catheter hub.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof encompasses the items listed thereafter and equivalents thereof as well as additional items. Unless limited otherwise, the terms "connected," "coupled," and "mounted," and variations thereof are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 1:
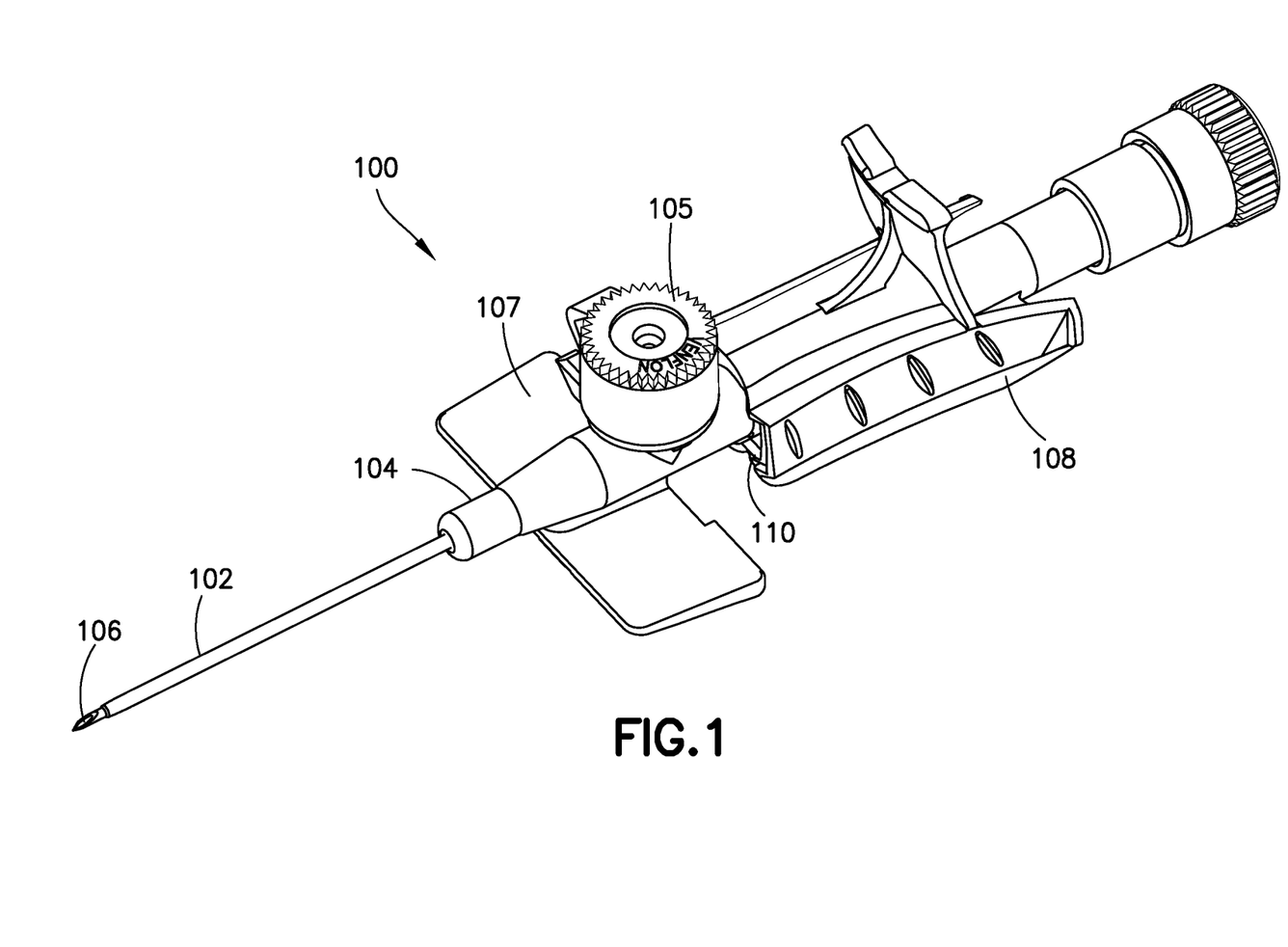
FIG. 1 is a top perspective view of a safety intravenous catheter assembly in accordance with an embodiment of the present invention.
Figure 2:
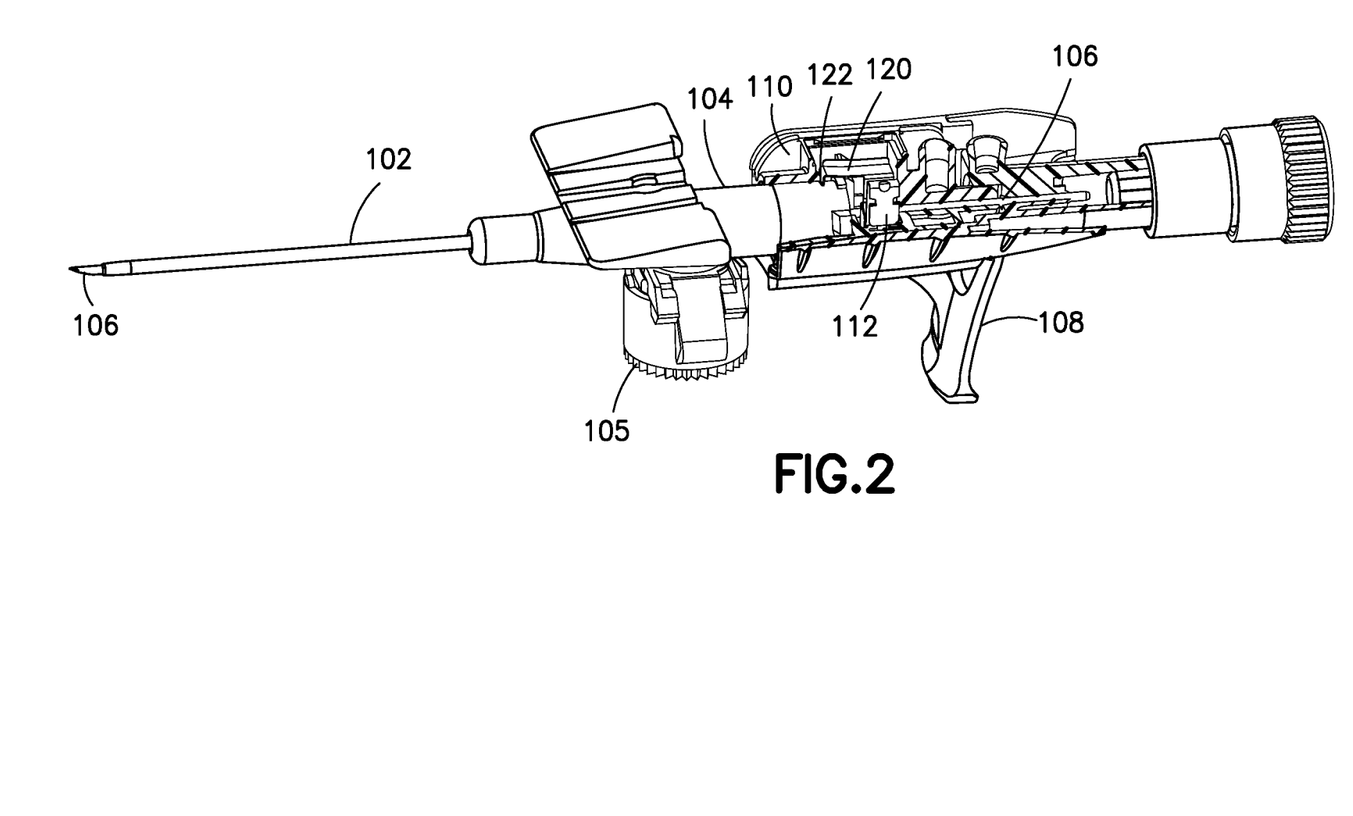
FIG. 2 is a bottom perspective partial view, partially in cross-section, of the catheter assembly of FIG. 1.

FIG. 1 is a top perspective view of a safety intravenous catheter assembly 100 embodiment of the present invention in a ready-to-use state, and FIG. 2 is a bottom perspective view, partially in cross-section, of the catheter assembly 100. The catheter assembly 100 includes a flexible plastic catheter 102 secured with a catheter hub 104. The catheter 102 and the catheter hub 104 form a first fluid pathway extending along a longitudinal axis of the catheter 102 and proximally terminating at a proximal port 103 (best shown in FIG. 9) adapted for connection with, for example, a Luer fitting, using Luer lugs or thread segments 128.

Additionally, according to one embodiment, the catheter hub 104 may include stabilization wings 107, which facilitate skin attachment after the catheter is inserted, for example, by securing the wings 107 to the skin with tape. The catheter hub 104 also may include a secondary side port 105 that forms a second fluid pathway in communication with the first fluid pathway. As described in U.S. Pat. No. 4,231,367, which is incorporated herein by reference in its entirety, the secondary side port 105 preferably includes a barrier, such as an internal tubular valve. The secondary side port 105 can be used, for example, to introduce additional fluid or medicament into a patient when the proximal port 103 is already in use. In this embodiment, the proximal end of the catheter hub 104 is substantially cylindrical. According to another embodiment, the catheter hub 104 does not include stabilization wings or a secondary side port.

Suitable materials for the flexible catheter 102 include, but are not limited to, thermoplastic resins such as fluorinated ethylene propylene (FEP), polytetrafluoroethylene (PTFE), polyurethane and the like. Preferably, the catheter 102 is formed from a thermoplastic hydrophilic polyurethane that softens with exposure to physiological conditions present in the patient's body. Suitable materials for the catheter hub 104 include, but are not limited to, thermoplastic polymeric resins such as polycarbonate, polystyrene, polypropylene, and the like.

The catheter assembly 100 also includes a hollow introducer needle 106 having a sharp distal tip defined by an upwardly facing bevel and a proximal end fixedly connected to a handle portion or needle hub 108 and disposed within the catheter 102. The introducer needle 106 is preferably formed from stainless steel and has a longitudinal axis generally parallel to the longitudinal axis of catheter and introducer needle assembly 100. The handle portion 108 may be formed from the same types of materials used to form catheter hub 104, but other materials could also be used to form the handle portion 108.

The catheter assembly 100 additionally includes a needle shield 110 and a resilient clip 112. According to one embodiment, the resilient clip 112 may be a V-shaped or W-shaped clip 112. Preferably, the resilient clip 112 is formed from stainless steel having a memory characteristic. It will be understood by one skilled in the art, however, that other flexible, strong, resilient materials could also be used to form the resilient clip 112, such as nitinol, co-polyesters, polypropylene, or other ductile plastics. The needle shield 110 may be formed from the same types of materials used to form catheter hub 104, but other materials could also be used to form the needle shield 110. The needle shield 110 has distal and proximal orifices 111 and 113 (best shown, respectively, in FIGS. 6 and 7) through which the introducer needle 106 is disposed.

Initially, in the illustrated ready-to-use state, the needle shield 110 is located within the handle portion 108, and a distal end 131 of the needle shield 110 is located within the catheter hub 104 to help center the needle shield 110 with respect to the catheter hub 104. This distal end 131 also provides stability for the introducer needle 106 and blood retention for the catheter hub 104 as the assembly 100 is being inserted into a patient.

Figure 7:
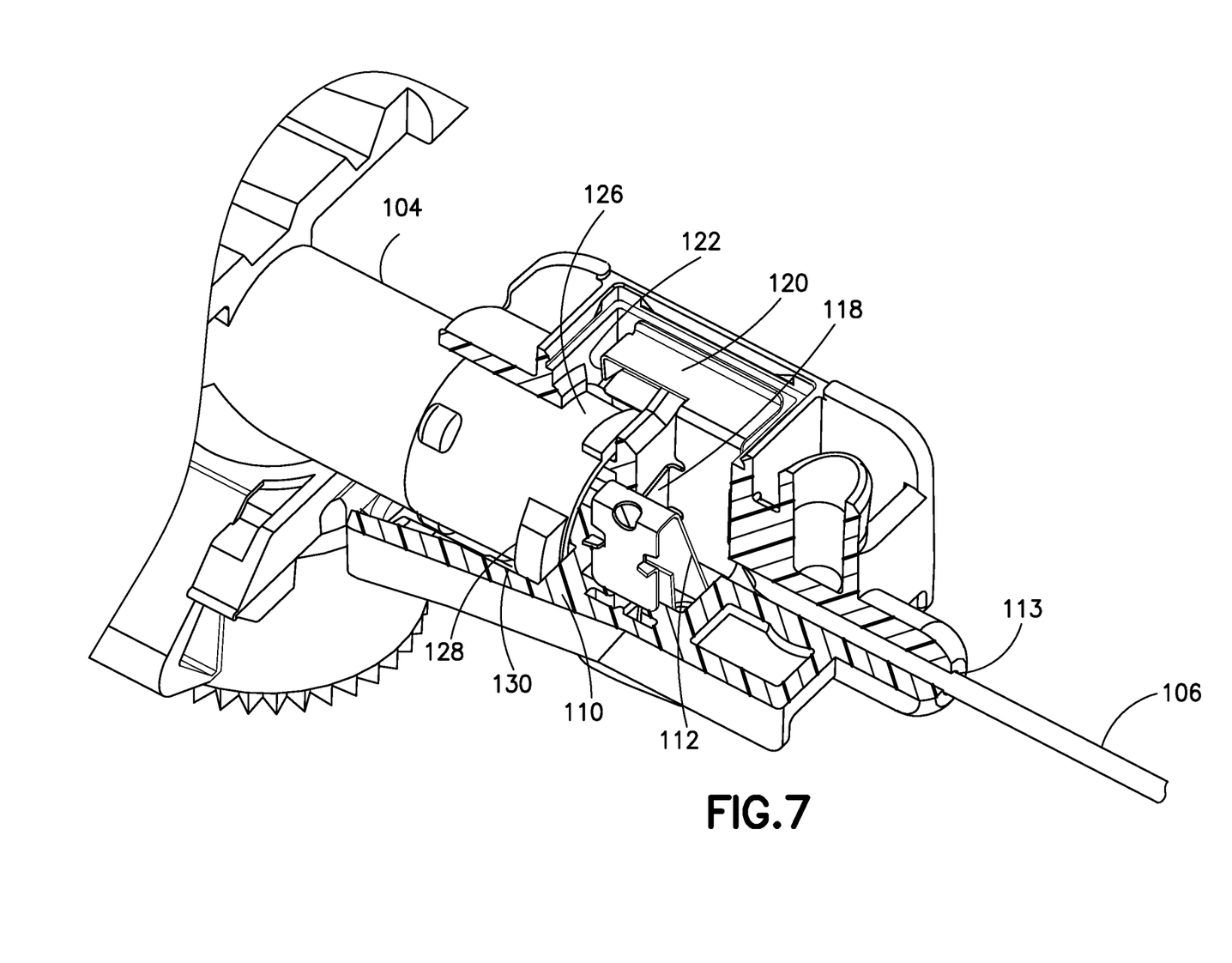
FIG. 7 is an enlarged bottom rear perspective view, partially in cross-section, of the catheter assembly of FIG. 1 after the resilient clip has been activated.

According to one embodiment, a flexible tether 134 connects the handle portion 108 and the needle shield 110. In all but FIG. 9, however, the tether 134 is omitted from the drawings for clarity. As subsequently discussed in greater detail, one skilled in the art will appreciate that other mechanisms for connecting the handle portion 108 and the needle shield 110 can be employed without departing from the scope of the present invention, for example, a bump on the introducer needle 106 and a corresponding catch feature in the resilient clip 112, or a washer type feature in the needle shield 110. As best shown in FIG. 7, slots 130 in the needle shield 110 cooperate with the Luer lugs 128 of the catheter hub 104 to prevent rotation of the needle shield 110 relative to the catheter hub 104.

Figure 3:
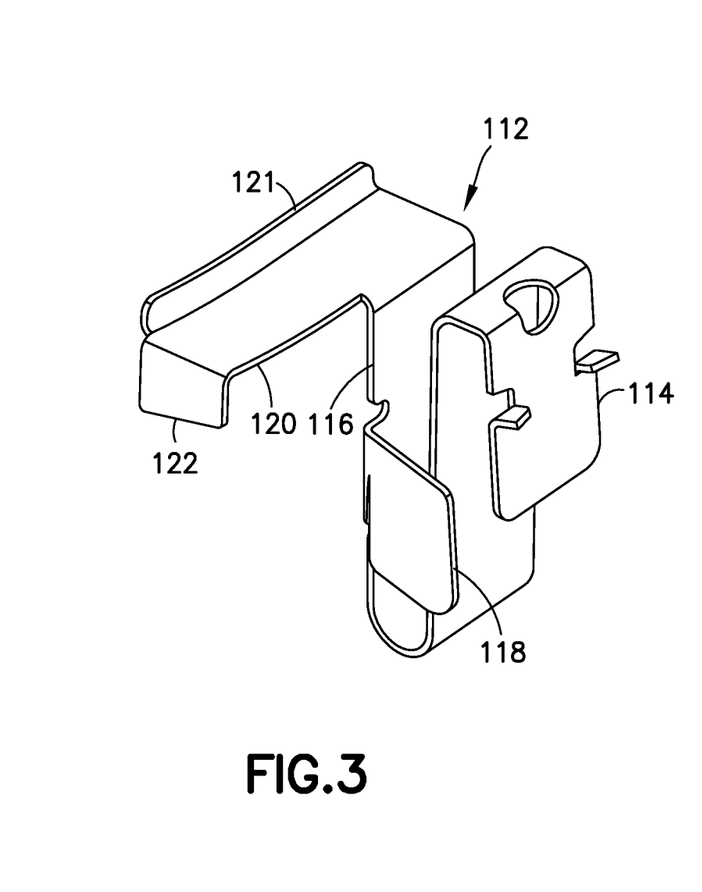
FIG. 3 is a bottom perspective view of a resilient clip of the catheter assembly of FIG. 1 in a first, biased position.
Figure 4:
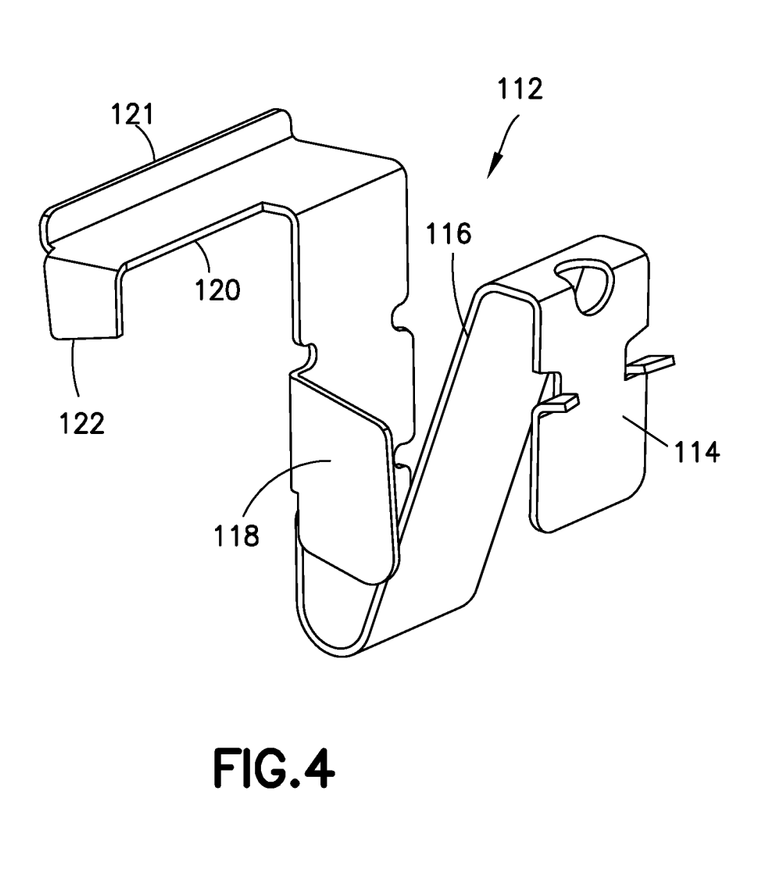
FIG. 4 is a bottom perspective view of the resilient clip of FIG. 3 in a second, unbiased or less biased position.

As subsequently described in greater detail regarding the operation of the catheter assembly 100, FIGS. 3 and 4 respectively illustrate the resilient clip 112 in a first, biased position, and in a second, unbiased or less biased position. According to one embodiment, in the second position, the resilient clip is not biased. As shown in FIGS. 3 and 4, the resilient clip 112 includes an anchoring portion 114 for anchoring the resilient clip 112 in the needle shield 110 so that when the resilient clip moves, it moves in a direction substantially perpendicular to the longitudinal direction of the introducer needle 106 and catheter 102.

The resilient clip 112 also includes an angled portion 116 with a needle blocker or transverse barrier 118 extending substantially perpendicular to the angled portion 116. According to one embodiment, the angled portion 116 is V-shaped. According to the embodiment shown, the needle blocker 118 extends from a distal portion of the angled portion 116. According to another embodiment, the needle blocker 118 extends from a proximal portion of the angled portion 116. As shown in FIGS. 3 and 4, the needle blocker extends from only one side of the V-shaped angled portion (i.e., one arm of the V-shape). According to yet another embodiment, a needle blocker 118 extends from each side of the angled portion 118 toward the middle of the angled portion 118. A cantilevered arm 120 also extends from the angled portion 116, and a finger or pawl 122 extends radially inward from the free, distal end of the cantilevered arm 120. The resilient clip 112 also includes a stiffening or reinforcing rib 121 for stiffening the cantilevered arm 120. Further details of a similar resilient clip can be found in the aforementioned U.S. Pat. No. 6,749,588.

Figure 5:
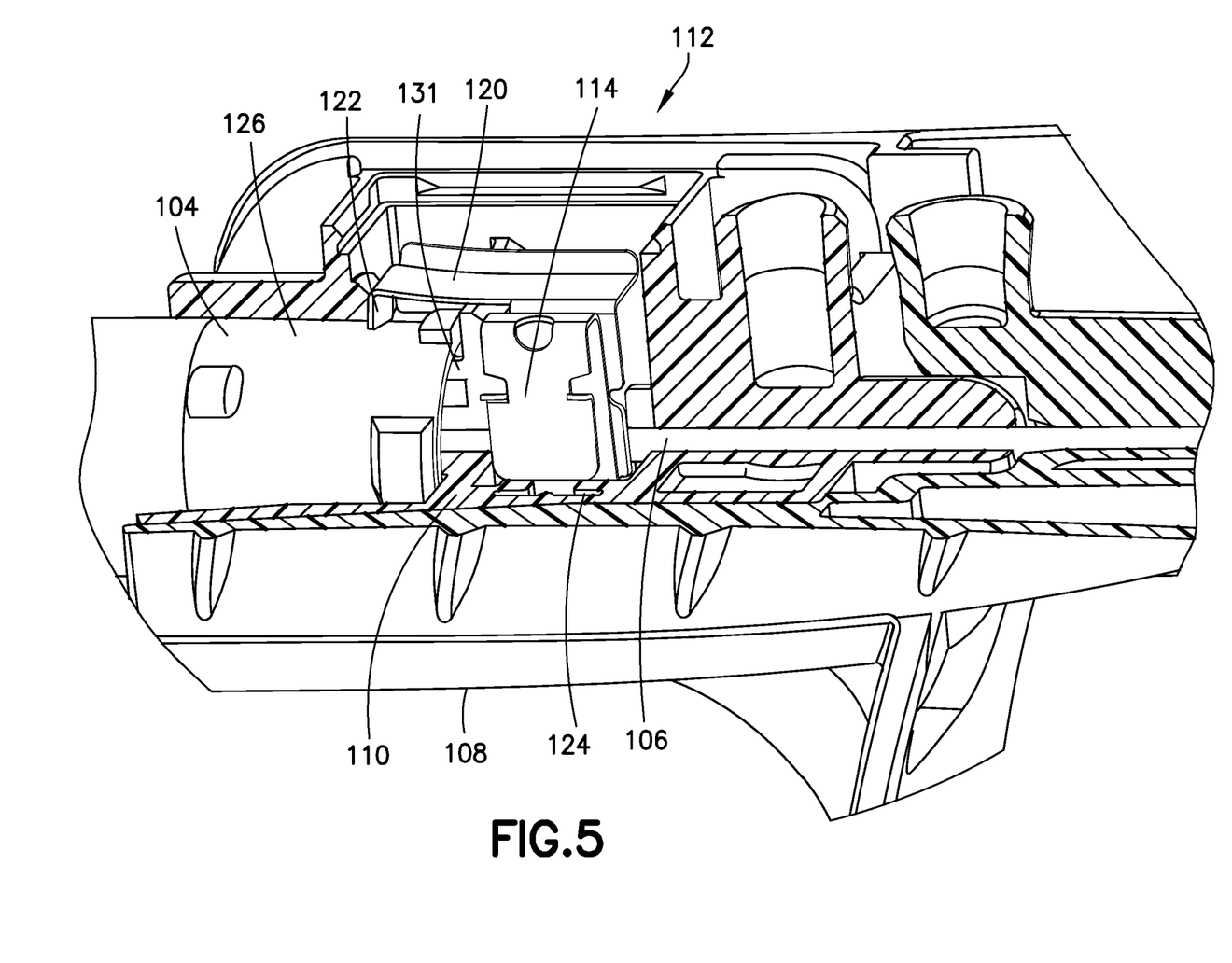
FIG. 5 is an enlarged bottom perspective view, partially in cross-section, of the catheter assembly of FIG. 1.
Figure 6:
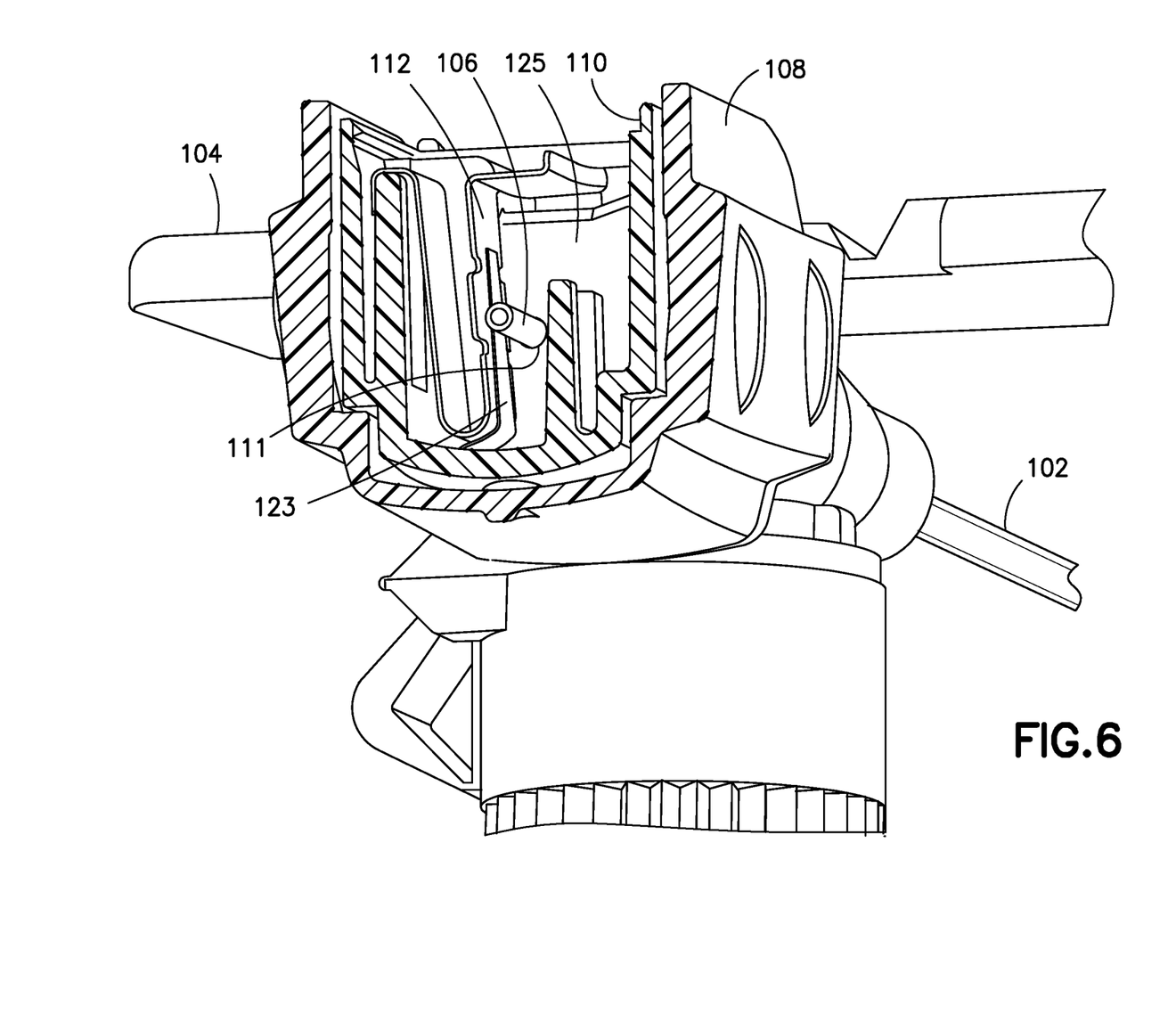
FIG. 6 is an enlarged partial rear perspective cross-sectional view of the catheter assembly of FIG. 1.

Referring to FIGS. 2, 5, and 6, in the illustrated ready-to-use state, the needle shield 110 is disposed at the proximal portion of the catheter hub 104. Anchoring portion 114 is fixedly disposed within a cavity 124 of the needle shield 110. According to one embodiment, the introducer needle 106 directly contacts a side of the angled portion 116 and holds the resilient clip 112 in the first or biased position.

The contact between the introducer needle 106 and the angled portion 116 of the resilient clip 112 generates a normal force at the interface. This normal force is opposed by the resulting normal forces between the introducer needle 106 and the distal and proximal orifices of the needle shield 110. In use, when the introducer needle 106 is proximally withdrawn, there will be friction forces at these three interfaces (i.e., between the introducer needle 106 and the distal and proximal orifices 111 and 113, and between the introducer needle 106 and the angled portion 116), and these reactive frictional forces are directed in the proximal direction. These frictional forces are proportional to the normal forces and the friction coefficients at the three interfaces. In addition to the direct contact friction (if any) between the needle shield 110 and the needle hub 108, and the proximal force generated by the tether 134 as the needle hub 108 is moved in the proximal direction, these frictional forces act to pull the needle shield 110 in the proximal direction. As subsequently described in greater detail, during withdrawal of the introducer needle 106, the summation of the forces on the needle shield 110 in the proximal direction is less than the summation of forces on the needle shield 110 in the distal direction (primarily generated by the interaction between the pawl 122 and an uninterrupted outer surface portion 126 of the catheter hub 104), thereby keeping the needle shield 110 in contact with the catheter hub 104 until the resilient clip 112 is activated, to avoid accidental exposure of the sharp distal end of the introducer needle 106.

According to another embodiment, as best shown in FIG. 6, a thin, flexible cantilevered extension or fin 123 extends radially inward from the needle shield 110 toward a central axis of the needle shield 110 to rest against a side of the angled portion 116 and intervene between the angled portion 116 and the introducer needle 106. The coefficient of friction between metal and metal is higher than the coefficient of friction between metal and the material or materials used to form the needle shield 110 and fin 123, for example, thermoplastic polymeric resins such as polycarbonate, polystyrene, polypropylene, and the like. Thus, in comparison to the introducer needle 106 directly contacting the angled portion 116 (with a coefficient of friction of about 0.5-0.6), the fin 123 reduces frictional contact with introducer needle 106 to a coefficient of friction of about 0.25-0.4. The introducer needle 106 holds the resilient clip 112 in the first or biased position via the fin 123.

According to another embodiment, to further reduce the friction between the fin 123 and the introducer needle 106, a lubricant, such as a silicone lubricant, is disposed on the fin 123. One skilled in the art will appreciate that other lubricants can be employed without departing from the scope of the present invention. Additionally, as shown in FIG. 6, the introducer needle extends through the orifice 111 in a distal portion 125 of the needle shield 110, which contacts and guides the introducer needle 106. An orifice 113 in a proximal portion of the needle shield 110 (visible in FIG. 7) also contacts and guides the introducer needle 106. According to one embodiment, the lubricant can be employed on the introducer needle 106 and/or the needle shield 110 (e.g., at the two orifices 111 and 113) to reduce friction between the needle shield 110 and the introducer needle 106.

The cantilevered arm 120 is flexed or bent to cause the pawl 122, which extends radially toward the catheter hub 104, to frictionally contact the uninterrupted outer surface portion 126 of the catheter hub 104 and thereby frictionally retain the needle shield 110 with the catheter hub 104. Additionally, contact between the distal end 131 of the needle shield 110 and the catheter hub 104, as well as contact between the Luer lugs 128 and the needle shield 110, may play a role in frictionally retaining the needle shield 110 with the catheter hub 104. The sum of these retaining forces is chosen to be greater than the sum of the previously described forces (e.g., those resulting from the proximally moving introducer needle 106) that tend to separate the needle shield 110 from the catheter hub 104.

The uninterrupted outer surface portion 126 is continuous, and substantially featureless. In other words, on the uninterrupted outer surface portion 126, no cavities or recesses or protrusions exist, so that the uninterrupted outer surface portion 126 is unbroken. The uninterrupted outer surface portion 126 may be smooth, or may be provided with a surface texture to enhance friction. According to one embodiment, the portion of the catheter hub 104 in which the uninterrupted outer surface portion 126 is disposed is substantially cylindrical.

In use, the doctor, nurse, other medical professional, or other user (hereinafter "user" for brevity) grasps the catheter assembly 100 and inserts the introducer needle 106 and catheter 102 into the patient's vein. After the catheter is placed in the patient's vein, the user begins to proximally withdraw the introducer needle using the needle hub 108 while holding the catheter 102 in position. Thus, the introducer needle 106 is moving relative to the catheter hub. Because of the differential between the greater frictional force of the pawl 122 interacting with the uninterrupted outer surface portion 126 and the sum of the lesser frictional force of the introducer needle 106 interacting with the resilient clip 112 and the needle shield 110, and the proximal forces in the tether 134, the pawl 122 retains the needle shield 110 with the catheter hub 104. In short, the frictional force generated by the contact between the pawl 122 and the uninterrupted outer surface portion 126 is greater than the force required to overcome the drag forces on the introducer needle 106. In other words, because the frictional resistance between the pawl 122 and the uninterrupted outer surface portion 126 is greater than the sum of the frictional resistance between the introducer needle 106 and the needle shield 110 and between the introducer needle 106 and the resilient clip 112, and the proximal force in the tether, the pawl 122 retains the needle shield 110 with the catheter hub 104 as the user proximally withdraws the introducer needle 106. Put another way, the releasable retention force resulting from the interaction between the pawl 122 and the uninterrupted outer surface portion 126 is only frictional, and this releasable frictional force frictionally retains the needle shield 110 with the catheter hub 104 against forces in the proximal direction generated as the introducer needle is withdrawn in the proximal direction.

Figure 8:
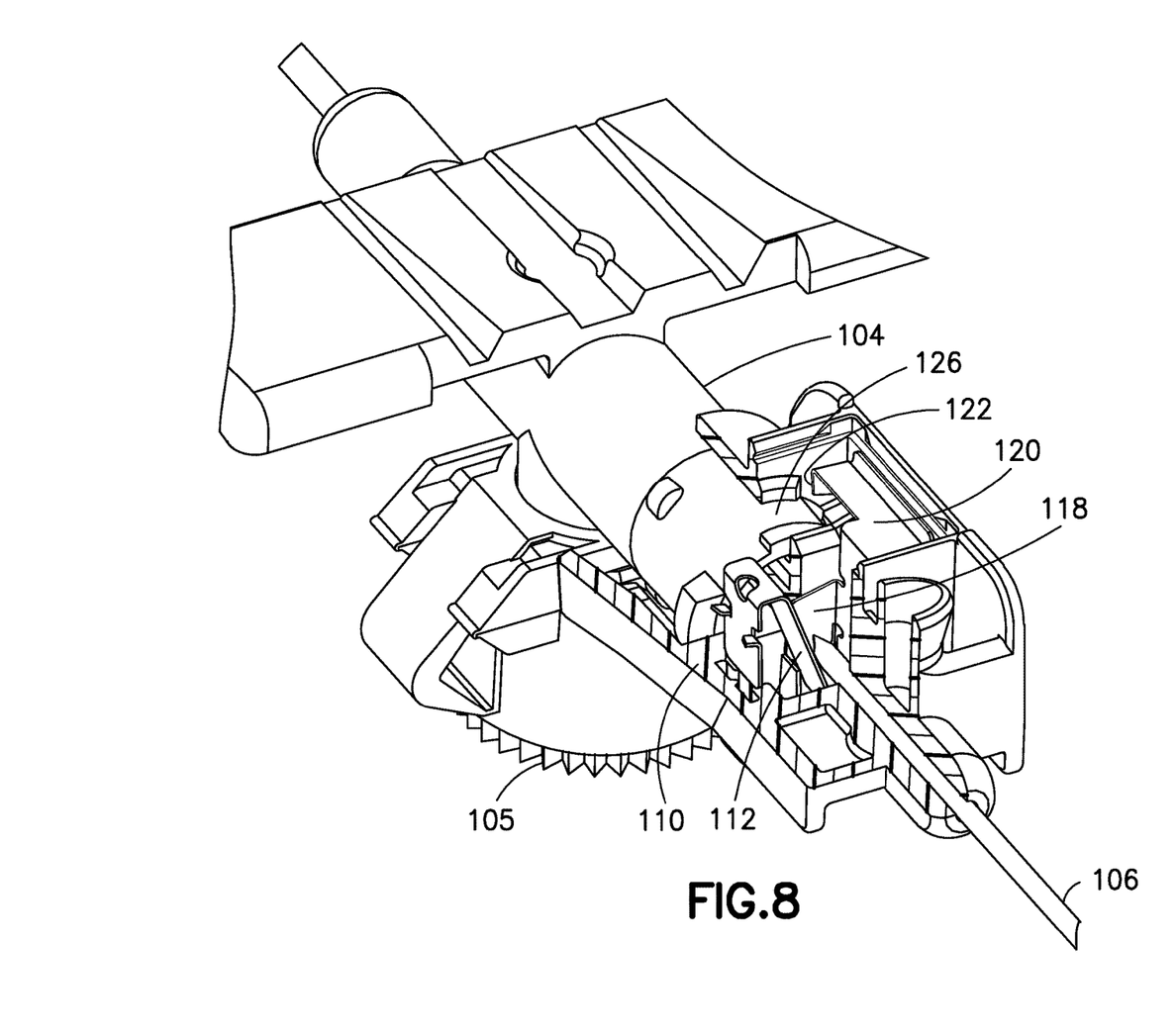
FIG. 8 is another enlarged bottom rear perspective view, partially in cross-section, of the catheter assembly of FIG. 1 after the resilient clip has been activated.

As shown in FIG. 7, once the user proximally withdraws the sharp distal end of the introducer needle 106 past the proximal edge of the resilient clip 112, the introducer needle 106 no longer compresses and holds the resilient clip 112 in the first, biased position. As a result, the resilient clip 112 activates and expands laterally in a direction substantially perpendicular to the longitudinal axis of the introducer needle 106 to the second, unbiased or less biased position (best illustrated in FIG. 4), causing the pawl 122 to move laterally out of contact with the uninterrupted outer surface portion 126. In addition, as shown in FIG. 8, the needle blocker 118 moves into a position across the longitudinal axis of the introducer needle 106, thereby preventing the user from distally displacing the introducer needle 106 past the needle blocker 118, and potentially re-exposing the sharp distal tip of the introducer needle 106. Thus, once the resilient clip 112 activates, the resilient clip 112 no longer frictionally retains the needle shield 110 with the catheter hub 104, and the resilient clip 112 prevents the introducer needle from displacing distally past the resilient clip 112.

As previously noted, the flexible tether 134 connects the needle shield 110 with the needle hub 108. As the user proximally displaces the introducer needle from the ready-to-use state illustrated in FIG. 1 to the clip-activated state illustrated in FIG. 7, the tether 134 expands substantially to its full length, preventing further proximal displacement of the introducer needle 106 relative to the needle shield 110. The needle blocker 118 prevents the introducer needle 106 from displacing distally relative to the needle shield 110 because the sharp distal tip of the introducer needle 106 is safely captured within the needle shield 110.

Figure 9:
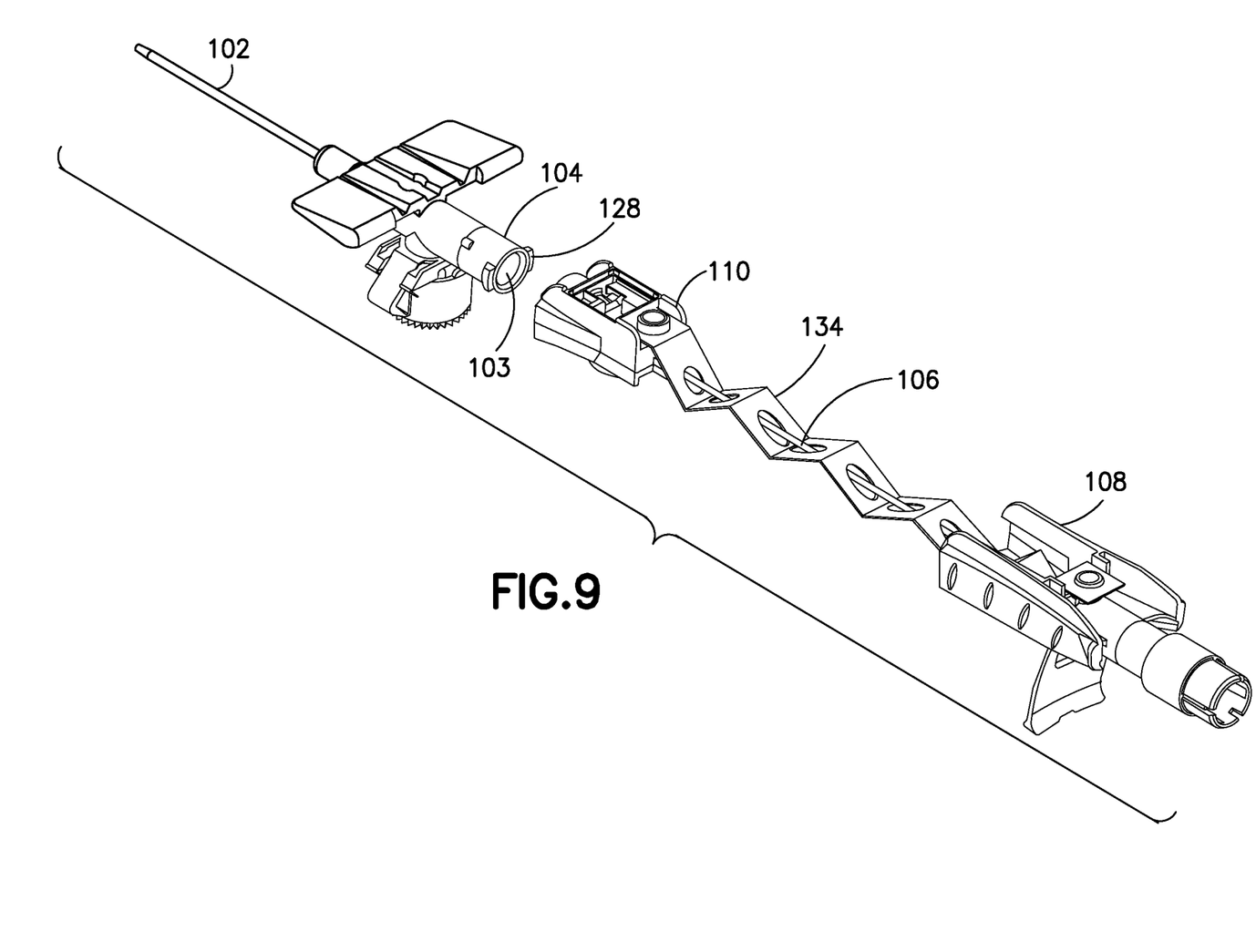
FIG. 9 is a bottom perspective view of the catheter assembly of FIG. 1 after a needle shield has been removed from a catheter hub.

Because the resilient clip no longer frictionally retains the needle shield 110 with the catheter hub 104, as the user continues to proximally displace the introducer needle 106, the proximal force applied by the fully extended tether overcomes any remaining friction and separates the needle shield 110 from the catheter hub 104, as shown in FIG. 9, thereby exposing the proximal port 103 for connection with medicament or other fluids.

In embodiments of the present invention, there is a balance of forces to provide the desired operation. For example, the frictional force of the contact between the pawl 122 and the uninterrupted outer surface portion 126 is chosen to exceed the remaining forces acting on the introducer needle 106 and the needle shield 110 during initial withdrawal of the introducer needle 106 to frictionally retain the needle shield 110 with the catheter hub 104. Thus, the goal is to increase the frictional force of the pawl-catheter hub interface and to decrease the frictional forces of the interactions of other device components. By achieving the desired balance of forces without resorting to recesses or undercuts on the catheter hub 104 to retain the catheter hub 104 with the needle shield 110 prior to activation of the resilient clip 112, the manufacturing of the assembly 100 can be simplified.

The frictional force ($F_f$) of the contact between the pawl 122 and the uninterrupted outer surface portion 126 is defined as being equal to $\mu N$, where $\mu$ is the coefficient of friction and N is the "normal force" or the force that is applied normal (perpendicular) to the uninterrupted outer surface portion 126. Thus, the frictional force can be increased by increasing the normal force applied by the pawl 122, by increasing the coefficient of friction of the uninterrupted outer surface portion 126, or both.

According to the embodiment shown in FIGS. 3 and 4, the edge of the pawl 122 that contacts the uninterrupted outer surface portion 126 is substantially linear. The shape of the pawl end, however, can be modified to optimize this contact. Although contact area is not a term in the frictional equation, optimizing the contact area can help provide a better mechanical interface between the two parts. This can be accomplished by shaping the pawl end to match the curvature of the uninterrupted outer surface portion 126. Different gauge insertion needles, however will compress the angled portion 116 of the resilient clip 112 to different degrees, and therefore, will affect the positioning of the pawl 122. Accordingly, the linear shape of the pawl 122 illustrated in FIGS. 3 and 4 represents a shape optimized to provide the desired normal force in combination with a range of different gauge introducer needles.

The pawl arm edge condition can be also be optimized. For example, the pawl edge can be sharpened, which can help by digging or biting into the softer plastic material of the catheter hub 104. In addition, the cantilevered arm 120 can be stiffened using features such as additional stiffening ribs or gussets that provide a higher normal force on the uninterrupted outer surface portion 126 as the cantilevered arm 120 is flexed, thus increasing the total frictional force. Further, the height or length of the pawl 122 can be adjusted to provide a greater pawl arm bias angle. If the pawl is taller, the cantilevered arm 120 must bend further, thereby providing a higher normal force, and thus, a greater frictional force.

The diameter of the catheter hub 104 at the uninterrupted outer surface portion can be increased to increase the bending of the cantilevered arm 120, thereby increasing the normal force and the resulting frictional force. The tip of the pawl 122 can also be covered with a material that has a higher coefficient of friction than that provided by the metal alone, for example, a rubber compound. In addition, the uninterrupted outer surface portion 126 can be formed, treated, or processed (e.g., machined) to provide more surface roughness, which can increase the coefficient of friction and the resulting friction force. Moreover, the uninterrupted outer surface portion 126 can have a coating or a second material injected over the plastic of the catheter hub 104 in a two-shot molding operation. For example, such a coating or second material can be a rubber or a soft touch plastic coating. The coefficient of friction between rubber and metal can approach one, and thereby more efficiently translate the normal force into a higher frictional retaining force.

The coefficient of friction between metal and plastic can range between 0.25 and 0.4. The predicted normal force of the pawl 122 on the uninterrupted outer surface portion 126 is approximately 0.4 Newtons to 1.4 Newtons, with an average around 0.8 Newtons to 1 Newton. In addition to the above-noted factors, other factors are also included in these predictions. For example, the initial friction (tip adhesions and catheter drag force) between the introducer needle 106 and the catheter 102, flexing of the cantilevered arm 120 during operation, other material deformation, the pawl 122 biting into the uninterrupted outer surface portion 126, and chatter between the pawl 122 and the uninterrupted outer surface portion 126, all add together to provide the pawl-catheter hub holding force.

There are several ways to reduce the frictional forces of the interactions of other device components. For example, as previously noted with respect to the fin 123, lubrication can be placed where device components interact. The coefficient of friction between plastic and plastic for static dry conditions can range between 0.3 and 0.4. With lubrication, this amount can be almost eliminated. A good candidate for such plastic-plastic lubrication is between the needle hub 108 and the needle shield 110.

In addition, if instead of a tether 134, a washer is used as the mechanism for retaining the needle shield 110 with the needle hub 108 (as subsequently described with respect to another embodiment), lubrication, washer edge finishing levels, and the finish of the introducer needle 106 can all be optimized to reduce friction. Further, the resilient clip 112 can be optimized for specific introducer needle gauge sizes. For example, for smaller gauge introducer needles 106, the resilient clip 112 is not as compressed as with larger introducer needles. Therefore, for smaller gauge introducer needles, the resilient clip 112 can be made thinner to provide the proper yielding force. The thinner resilient clip 112 will provide less normal force to the introducer needle 106. For larger gauge introducer needles, the resilient clip 112 endures greater lateral displacement. The material thickness and the hardness of the resilient clip 112 play a role in providing the proper restoring force, but consequently the force applied to the needle increases.

Figure 10:
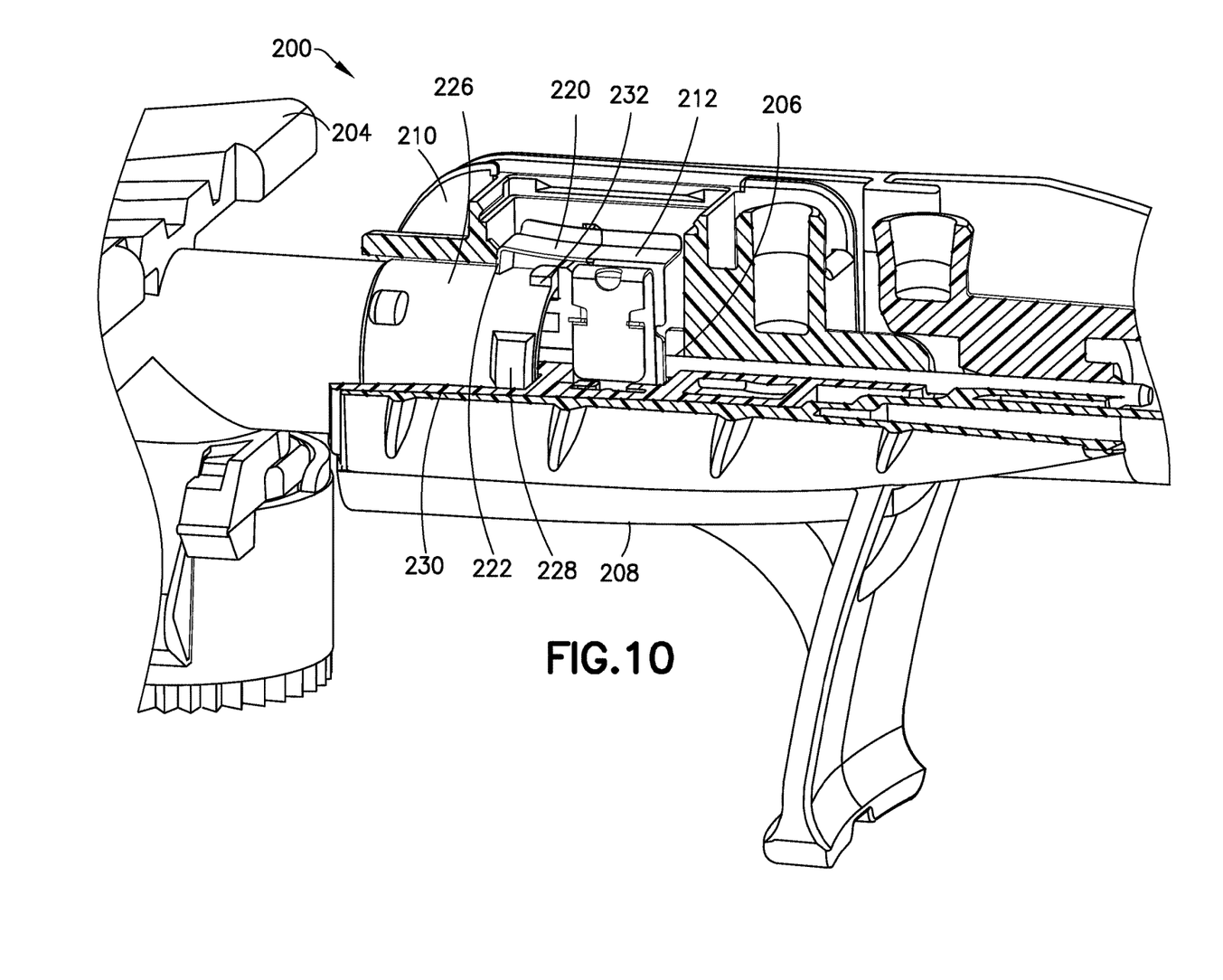
FIG. 10 is an enlarged bottom perspective view, partially in cross-section, of a catheter assembly in accordance with another embodiment of the present invention.

FIG. 10 is an enlarged bottom perspective view, in partial cross-section, of another catheter assembly embodiment of the present invention. For this and other subsequently-described embodiments, all reference characters designating corresponding parts of the embodiments are the same as those in the embodiment of FIGS. 1-9, except that they are in a different series, for example, in the 100 series, or the 200 series. The differences of the second embodiment with respect to the first embodiment will now be described.

As discussed, the protection of the user from accidental needle sticks is a concern. Thus, a disabling feature 232 in the form of an integral, radially extending projection is disposed at the proximal end of the catheter hub 204 in the event that the user improperly uses the device in such a way that would result in the resilient clip 212 not activating. On the other hand, the disabling feature 232 cannot prevent the needle shield 210 and the catheter hub 204 from separating. It is in fact possible, by applying sufficient force, to separate the needle shield 210 from catheter hub 204, despite the disabling feature 232, and in this case the needle tip is not entrapped by the needle blocker 218 (not shown) because clip 212 does not activate.

Initially, the pawl 222 contacts the uninterrupted outer surface portion 226 at a distance from the disabling feature 232, which is axially aligned with the pawl 222 when the resilient clip 112 is in the first, biased position. If during the withdrawal of the introducer needle 206, the user mistakenly grasps the needle shield 210, instead of the needle hub 208, and moves the needle shield 210 relative to the catheter hub a far enough distance such that the pawl 222 contacts the disabling feature 232, the disabling feature 232 will disable the device 200 by resisting further movement of the needle shield 210 relative to the catheter hub 204. As in the first embodiment, slots 230 in the needle shield 210 cooperate with the lugs 228 to prevent rotation of the needle shield 210 relative to the catheter hub 204.

With enough force, however, the pawl 222 can be forced proximally past the disabling feature 232, resulting in the accidental exposure of the sharp distal needle tip, because the resilient clip will not activate. According to one embodiment, the force required to overcome or defeat the disabling feature 232 in this way is between 14-17 Newtons (3.1-3.8 lbs$_f$). This force is substantially greater than the force required to properly withdraw the introducer needle 206 from the catheter hub 204, which is approximately 0.03-0.06 Newtons (0.007-0.013 lbs$_f$). Thus, although it is possible to defeat the disabling feature 232, it serves as a tactile and/or audible indicator of improper use to the user, as well as an impediment to such improper use. As in the previously described embodiment, it is the frictional forces resulting primarily from interaction between the pawl 222 and the uninterrupted outer surface portion 226, rather than any interaction between the pawl 222 and the disabling feature 232, that retains the needle shield 210 with the catheter hub 204 against the forces caused by the introducer needle 206 withdrawing from the catheter 202.

Figure 11:
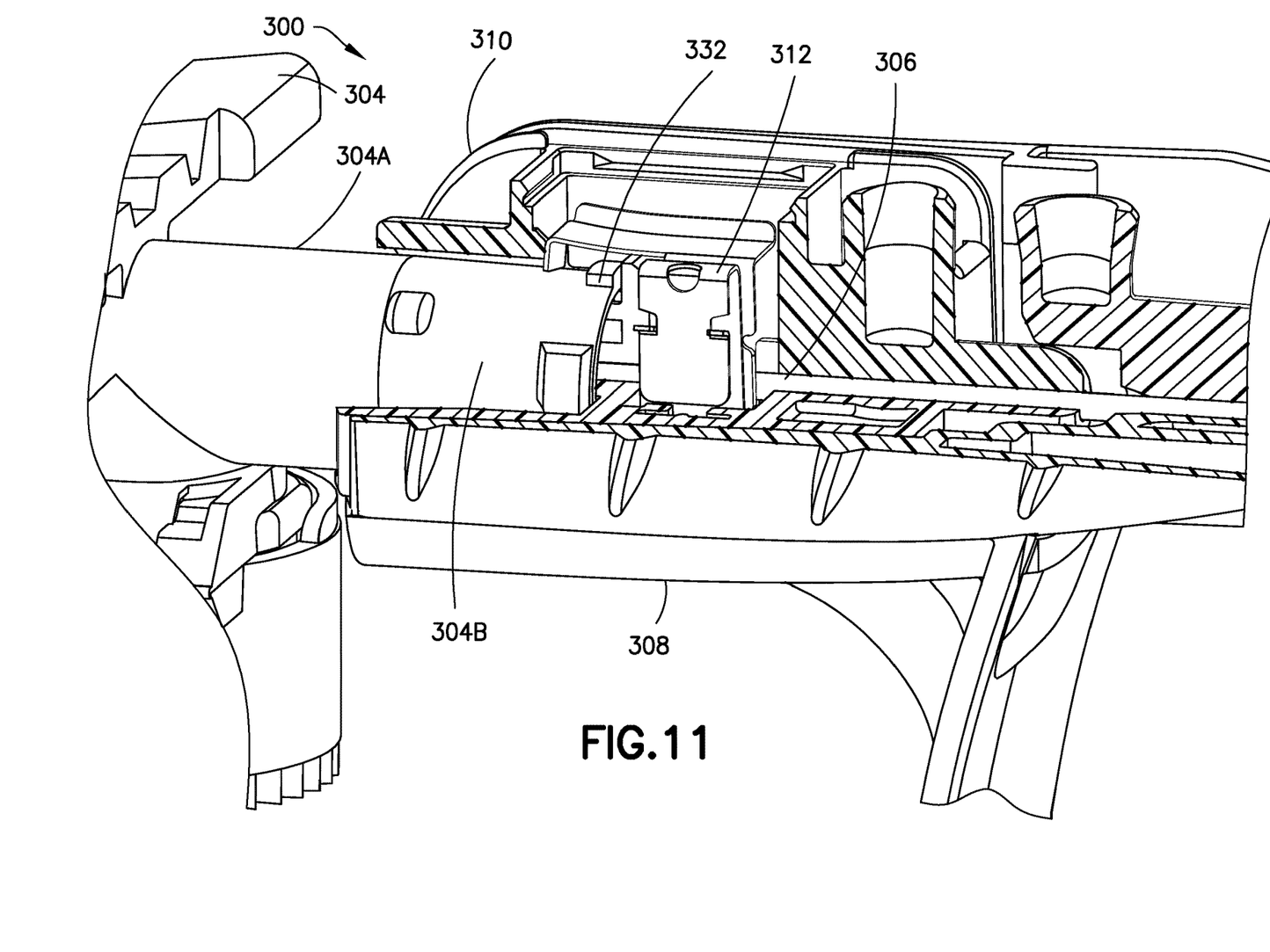
FIG. 11 is an enlarged bottom perspective view, partially in cross-section, of a catheter assembly in accordance with yet another embodiment of the present invention.

In the embodiments of FIGS. 1-10, the shape of the proximal end of the catheter hub is substantially cylindrical. One skilled in the art will appreciate, however, that other shapes can be employed without departing from the scope of the present invention. For example, as shown in FIG. 11, the intravenous catheter assembly 300 includes a catheter hub 304 with a cylindrical central section 304A and a proximal section 304B that tapers proximally. According to one embodiment, the taper is approximately 1.3° measured from a central longitudinal axis of the catheter hub 304 (approximately 2.6° total included angle). In the embodiment shown in FIG. 11, the uninterrupted outer surface portion 326 is disposed on the tapered proximal section 304B. According to one embodiment, with respect to the central longitudinal axis of the catheter hub 304, the height of the disabling feature 332 above the axis is substantially the same as that of the cylindrical central section 304A.

Other shapes can also be used for the proximal end of the catheter hub. For example, the proximal end can be inversely tapered (with a diameter becoming larger toward the proximal end), or the proximal end can be cylindrical but have a reduced diameter compared to a central section of the catheter hub. Additionally, in cross-section, the proximal end of the catheter hub can be triangular, square, pentagonal, hexagonal, or can have any other regular or irregular geometric shape. In addition, the shape, length, thickness, and positioning of the cantilevered arm of the resilient clip, as well as the shape and thickness of the pawl, and the surface texture of the catheter hub can be varied to provide the desired frictional interaction between the pawl and the catheter hub. According to one embodiment, the texture of the uninterrupted outer surface portion is an electrical discharge machined (EDM) surface texture finish.

Figure 12:
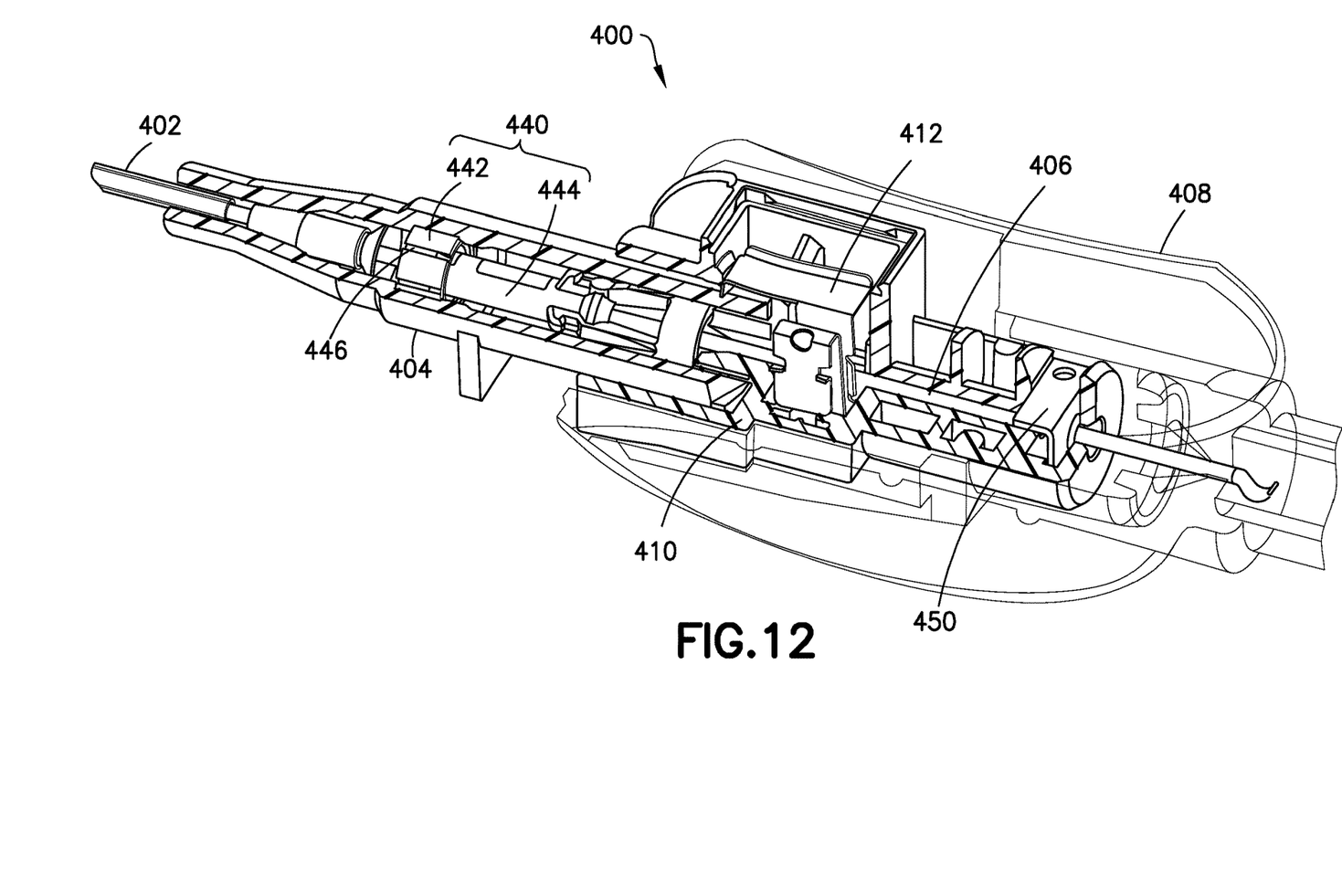
FIG. 12 is an enlarged bottom perspective view, partially in cross-section, of a catheter assembly in accordance with yet another embodiment of the present invention.

In the embodiment shown in FIG. 12, the catheter hub 404 does not include stabilization wings, but does include a blood control mechanism 440 for selectively controlling activation of fluid flow in the intravenous catheter assembly 400. The blood control mechanism 440 includes a septum 442 and a hollow actuator 444. Briefly, the septum 442 seals the catheter hub 404 until the user distally displaces the actuator 444, for example, by connecting a Luer connector with the catheter hub 404. Such displacement opens the septum 442 and permits fluid flow through the catheter hub 404. Additionally, the septum includes axial channels 446, which are sized to permit passage of air, but not fluid. Blood control mechanisms are described in greater detail, for example, in U.S. Pat. No. 8,388,583, which is assigned to the same assignee as the present application and which is herein incorporated by reference in its entirety.

In the embodiment shown in FIG. 12, the resilient clip is disposed proximally with respect to the septum 442. In addition, in the assembly 400, rather than a tether, the assembly 400 includes a washer 450 and the introducer needle 406 includes a radial protrusion (not shown) near its distal tip that engages the washer 450 subsequent to the distal tip of the introducer needle 406 proximally passing the resilient clip 412 during needle withdrawal. The through-hole in the washer 450 is not large enough to permit passage of the radial protrusion therethrough. Accordingly, after the sharp distal tip of the introducer needle 406 proximally passes the resilient clip 412, the resilient clip 412 activates and displaces laterally to the second position, disposing the needle blocker 418 in the path of the introducer needle and preventing subsequent distal displacement of the introducer needle 406 relative to the needle shield 412. Because the washer 450 prevents further proximal displacement of the introducer needle 406 relative to the needle shield 412, the needle shield captures the sharp distal tip of the introducer needle 406, protecting against accidental needle sticks.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

What is claimed is:

1. A catheter and introducer needle assembly, comprising:
   a catheter;
   a catheter hub in fluid communication with the catheter, the catheter hub having an outer surface portion, a flange disposed proximally of the outer surface portion, and a disabling feature circumferentially spaced from the flange and extending radially outward from a proximal portion of the catheter hub;
   an introducer needle disposed in the catheter;
   a needle shield; and
   a resilient clip adapted to flex between a first position and a second position, the resilient clip having a cantilevered arm with a pawl;
   wherein, in the first position, the cantilevered arm of the resilient clip is flexed so that the pawl frictionally contacts the outer surface portion of the catheter hub to retain the needle shield with the catheter hub, and in the second position, the pawl no longer frictionally contacts the outer surface portion, thereby permitting displacement of the needle shield relative to the catheter hub; and
   wherein the disabling feature is aligned with and spaced apart from the pawl when the resilient clip is in the first position.

2. The assembly according to claim 1, wherein:
   when a distal end of the introducer needle extends distally past the resilient clip, the resilient clip is held to one side of the introducer needle in a biased position; and
   upon the distal end of the introducer needle being proximally withdrawn past the resilient clip, the resilient clip flexes to an unbiased or less biased position in which it no longer frictionally retains the needle shield with the catheter hub.

3. The assembly according to claim 2, wherein the resilient clip comprises an angled portion having a needle blocker extending therefrom; and
   wherein when the resilient clip flexes to the unbiased or less biased position, the needle blocker is disposed to prevent distal displacement of the distal end of the introducer needle distally past the needle blocker.

4. The assembly according to claim 1, wherein the resilient clip comprises an angled clip, at least a portion of which is movably disposed within the needle shield, the angled clip having an angled portion with the cantilevered arm extending therefrom.

5. The assembly according to claim 1, wherein the catheter hub includes a proximal port adapted for fluid communication with the catheter and connection with a Luer connector.

6. The assembly according to claim 5, wherein the catheter hub comprises a secondary side port adapted for fluid communication with the catheter when the proximal port is in use.

7. The assembly according to claim 1, further comprising:
   a needle hub disposed at the proximal end of the introducer needle; and
   a flexible tether connecting the needle shield and the needle hub.

8. The assembly according to claim 1, further comprising a flexible cantilevered fin extending radially from the needle shield toward a central axis of the needle shield;

wherein the fin is disposed between the introducer needle and the resilient clip.

9. The assembly according to claim 1, further comprising a septum and an actuator disposed within the catheter hub;
   wherein the septum is pierceable by actuator displacement; and
   the resilient clip is disposed proximal to the septum.

10. The assembly according to claim 1, wherein:
    a normal force applied by the pawl on the outer surface portion of the catheter hub is in the range of 0.4 to 1.4 Newtons; and
    a coefficient of friction between the pawl and the outer surface portion of the catheter hub is in the range of 0.25 to 0.4.

11. The assembly according to claim 1, wherein the outer surface portion of the catheter hub comprises an uninterrupted outer surface portion.

12. A catheter and introducer needle assembly, comprising:
    a catheter hub having a fluid path, an outer surface portion, a flange disposed proximally of the outer surface portion, and a disabling feature circumferentially spaced from the flange and extending radially outward from a proximal portion of the catheter hub;
    a catheter communicating with the fluid path; and
    an introducer needle assembly, comprising:
      an introducer needle;
      a needle shield selectively disposed at the catheter hub, the introducer needle being disposed through the needle shield, the catheter hub, and the catheter; and
      a resilient clip movably disposed within the needle shield and having a cantilevered arm extending therefrom with a pawl at a free end of the cantilevered arm, the cantilevered arm being flexed so that the pawl frictionally contacts the outer surface portion and frictionally retains the needle shield with the catheter hub;
    wherein the disabling feature is aligned with and spaced apart from the pawl when the resilient clip is flexed so that the pawl frictionally contacts the outer surface portion.

13. The assembly according to claim 12, wherein:
    the introducer needle holds the resilient clip in a first compressed position until a distal end of the introducer needle proximally passes the resilient clip; and
    subsequent to the distal end of the introducer needle proximally passing the resilient clip, the resilient clip expands laterally to an unbiased or less biased position in which the pawl no longer frictionally contacts the outer surface portion and the resilient clip no longer frictionally retains the needle shield with the catheter hub.

14. The assembly according to claim 12, wherein the resilient clip comprises an angled clip having an angled-portion with the cantilevered arm extending therefrom.

15. The assembly according to claim 12, the catheter hub includes a proximal port adapted for fluid communication with the catheter and connection with a Luer connector.

16. The assembly according to claim 12, further comprising a needle hub fixedly disposed at a proximal end of the introducer needle, wherein a flexible tether connects the needle shield and the needle hub.

17. The assembly according to claim 12, further comprising a flexible cantilevered fin extending radially from the needle shield toward a central axis of the needle shield;
    wherein the fin is disposed between the introducer needle and the resilient clip.

18. The assembly according to claim 12, further comprising a septum and an actuator disposed within the catheter hub;
    wherein the septum is pierceable by actuator displacement; and
    the resilient clip is disposed proximal to the septum.

19. The assembly according to claim 12, wherein:
    a normal force applied by the pawl on the outer surface portion is in the range of 0.4 to 1.4 Newtons; and
    a coefficient of friction between the pawl and the outer surface portion is in the range of 0.25 to 0.4.

20. The assembly according to claim 12, wherein the outer surface portion of the catheter hub comprises an uninterrupted outer surface portion.

* * * * *